United States Patent [19]
Aoki

[11] Patent Number: 5,405,928
[45] Date of Patent: Apr. 11, 1995

[54] METHOD OF PREPARING (METH)ACRYL GROUP-CONTAINING ORGANOSILOXANES

[75] Inventor: Shunji Aoki, Annaka, Japan

[73] Assignee: Shin-Etsu Chemical Co., Ltd., Tokyo, Japan

[21] Appl. No.: 205,470

[22] Filed: Mar. 4, 1994

[30] Foreign Application Priority Data

Mar. 5, 1993 [JP] Japan .................. 5-070812

[51] Int. Cl.$^6$ .......................... C08G 77/08
[52] U.S. Cl. ..................... 528/12; 528/23; 528/32
[58] Field of Search .............. 528/12, 23, 32

[56] References Cited

U.S. PATENT DOCUMENTS 4,070,313  1/1978  Papa ........................ 528/25
5,051,473  9/1991  Tabuchi et al. ............. 528/12

*Primary Examiner*—Melvyn I. Marquis
*Attorney, Agent, or Firm*—Millen, White, Zelano & Branigan

[57] ABSTRACT

A method of preparing (meth)acryl group-containing organosiloxanes, wherein only the alkoxy group(s) of a (meth)acryl group-containing alkoxysilane compound is(are) selectively hydrolyzed using a cation exchange resin as acid catalyst.

10 Claims, No Drawings

METHOD OF PREPARING (METH)ACRYL GROUP-CONTAINING ORGANOSILOXANES

FIELD OF THE INVENTION

The present invention relates to a method of preparing acryl or methacryl group-containing organosiloxanes (which are abbreviated as (meth)acryl group-containing organosiloxanes, hereinafter) and, more particularly, to a method of preparing (meth)acryl group-containing organosiloxanes with ease in one reaction vessel without any accompanying side-reaction.

BACKGROUND OF THE INVENTION

As one of the methods for preparing (meth)acryl group-containing organosiloxanes, there is known the method of conducting a hydrosilylation reaction between SiH group-containing organopolysiloxanes and alkenyl group-containing (meth)acrylic compounds in the presence of a platinum catalyst (as disclosed in Japan Tokkai No. 48-47998). Herein, the term "Japan Tokkai" stands for an unexamined published Japanese patent application.

However, the above-cited method has a problem wherein the yield rate of the intended (meth)acryl group-containing organosiloxane is markedly reduced due to the condition that part of the SiH groups can react on the (meth)acryl groups, apart from the case in which the SiH groups selectively react only on the alkenyl group contained in a (meth) acrylic compound to effect hydrosilylation.

The problem of reaction selectivity in the above-described hydrosilylation can be solved by adopting the method of first causing (meth)acrylic acid to react on an epoxy group-containing siloxane and then causing (meth)acrylic acid chloride to react on the thus obtained product in the presence of a hydrogen chloride scavenger (as disclosed in Japan Tokkai No. 63-135426).

In such a method, however, it is necessary to prepare in advance the epoxy group-containing siloxane by conducting the hydrosilylation reaction between the SiH group-containing siloxane and the alkenyl group-containing epoxy compound in the presence of a platinum catalyst. This method also, therefore, has a disadvantage in that the preparation requires several reaction steps.

Further, there is known another method in which the alkoxy group(s) of a (meth)acryloxy group-containing alkoxysilane is(are) hydrolyzed using a highly nucleophilic acid as catalyst.

The above-cited method, however, is accompanied by a side-reaction such that the (meth)acrylate moiety is also hydrolyzed. Therefore, it suffers from a defect that the by-products arising from the side-reaction exert bad influences upon the reactivity of the intended compound in the next reaction step and upon physical properties of the final product obtained therefrom.

SUMMARY OF THE INVENTION

As a result of our intensive studies for solving the above-described problems, it has been found out that only the alkoxy group(s) of a (meth)acryl group-containing alkoxysilane can be selectively hydrolyzed when a cation exchange resin is used as acid catalyst in place of highly nucleophilic acids, thereby achieving the present invention.

An object of the present invention is, therefore, to provide a method of preparing (meth)acryl group-containing organosiloxanes with ease in one reaction vessel without any accompanying side-reaction.

The above-described object is attained by a method of preparing (meth)acryl group-containing organosiloxanes in which only the alkoxy group(s) of a (meth)acryl group-containing alkoxysilane compound (which is simply called "a silane compound", hereinafter) is(are) selectively hydrolyzed using a cation exchange resin as acid catalyst.

DETAILED DESCRIPTION OF THE INVENTION

The present invention is described below in detail.

A silane compound used as a starting material in the present method can be properly chosen from silane compounds containing both (meth)acryl and alkoxy groups. In particular, it is preferred to use those having the following general formula:

$$A_a SiR^1{}_b (OR^2)_c.$$

In the above formula, A represents a monovalent hydrocarbon residue containing a (meth)acryl group. The hydrocarbon residue preferred as A is a functional group represented by the general formula; $CH_2=CR^3COO(CH_2)_d-$ (wherein $R^3$ is a hydrogen atom or a methyl group, and d is an integer of from 1 to 6). Specific examples of A as the functional group include $CH_2=CHCOO(CH_2)_3-$, $CH_2=C(CH_3)COO(CH_2)_3-$, $CH_2=CHCOOCH_2-$, $CH_2=C(CH_3)COOCH_2-$ and so on.

Further, a and c are each an integer of from 1 to 3, and b is 0, 1 or 2; provided that $a+b+c$ is 4. However, it is preferable for "a" to be 1, because the corresponding silane compounds are easily accessible.

$R^1$ represents an alkyl group containing 1 to 10 carbon atoms or an aryl group. It is desirable for ease of access that $R^1$ be methyl, ethyl or phenyl group. $R^2$ represents an alkyl group containing 1 to 6 carbon atoms, preferably a methyl, ethyl or propyl group, in order that the corresponding silane compounds are easily accessible and have high reactivity.

The silane compounds as described above may be used alone, or as a mixture of two or more thereof. In particular, the silane compounds represented respectively by the formulae; $CH_2=CHCOO(CH_2)_3SiCH_3(OCH_3)_2$, $CH_2=CHCOO(CH_2)_3Si(OCH_3)_3$, $CH_2=CHCOO(CH_2)_3Si(CH_3)_2(OCH_3)$, $CH(CH_3)=CHCOO(CH_2)_3Si(OCH_3)_3$, $CH(CH_3)=CHCOO(CH_2)_3SiCH_3(OCH_3)_2$ and $CH(CH_3)=CHCOO(CH_2)_3Si(CH_3)_2(OCH_3)$, and the like can be used to greater advantage.

According to the preparation method of the present invention, a cation exchange resin selectively reacts as an acid catalyst only upon the alkoxy group(s) contained in the above-illustrated silane compounds, so that the ester moiety (—COO—) does not undergo hydrolysis. Therefore, the (meth)acryl group-containing organosiloxanes obtained in accordance with the present preparation method are high in purity and yield rate, compared with those prepared by the conventional method using a highly nucleophilic acid as acid catalyst.

When a cation exchange resin of $H^+$ type is used, the activity thereof in the present reaction is hardly influenced by the species of functional groups it contains, the acid group content thereof and the surface area thereof. Therefore, the cation exchange resin for the present invention can be properly chosen from those of H+type.

The amount of the cation exchange resin used is desirably in the range of 0.1 to 20 parts per 100 parts of the silane compound. As for the water, it is required to use it in an amount sufficient to thoroughly hydrolyze the silane compound. In general it is desirable to use water in an amount of 1 to 200 parts per 100 parts of the silane compound.

Further, it is allowable to mix the present silane compounds as illustrated above with other alkoxy group-containing silane compounds, such as those represented by the general formula, $R^1_{(4-e)}Si(OR^2)_e$ (wherein $R^1$ and $R^2$ have the same meanings as described above, respectively; and e is an integer of from 1 to 4), and to simultaneously hydrolyze them, if desired. In the hydrolysis, there is no particular restriction as to the ratio between the present silane compounds and others used. Also, a polymerization inhibitor can be added to the reaction solution in order to control the polymerization. Specific examples of an alkoxy group-containing silane compound as cited above include $(CH_3)_2Si(OCH_3)_2$, $(C_6H_5)_2Si(OCH_3)_2$, $(CH_3)(C_6H_5)Si(OCH_3)_2$, $(CH_3)Si(OCH_3)_3$, $(C_6H_5)Si(OCH_3)_3$, $Si(OC_2H_5)_4$, $(CH_3)_3Si(OCH_3)$, and mixtures of two or more thereof.

In conducting the hydrolysis reaction, a cation exchange resin is added in advance of the present silane compound(s) alone or the silane compound mixture described above, and thereinto is poured water; or the mixture of the silane compound(s) with water is passed through a column packed with a cation exchange resin.

In general, the hydrolysis reaction can progress satisfactorily under room temperature. In case the evolution of heat is violent upon the reaction, however, cooling the reaction system to 0°–20° C. will suffice for moderating the heat evolution. On the other hand, i.e., in case of the reaction's making little progress at room temperature, heating the reaction system up to 40°–100° C. will suffice to promote the reaction. The present hydrolysis reaction is not particularly restricted in its reaction time.

At the conclusion of the hydrolysis, it is desirable that the alcohol ($R^2OH$) produced in the reaction system and excess water be removed. In order to remove them, the reaction mixture is heated, if necessary, under reduced pressure so that they may be distilled off. This distillation step for the removal is not particularly restricted as to the heating temperature and the degree of pressure reduction. As a general guide, the temperature may be chosen from the range of 40° to 120° C. and the pressure from the range of 5 to 200 Torr.

After the removal of the alcohol and the excess water, the condensation reaction takes place between any two of the SiOH groups and $SiOR^2$ groups remaining in the reaction system to produce the intended (meth)acryl group-containing organosiloxane. In order to complete the condensation reaction, a certain catalyst can be added to the reaction system, if needed. Specific examples of such a catalyst include metallic salts such as zinc caprylate, iron caprylate, tin caprylate, etc., alkyl group-containing tin salts such as dibutyltin dicaprylate, dioctyltin diacetate, etc., acids such as sulfuric acid, hydrochloric acid, acetic acid, trichloroacetic acid, methanesulfonic acid, trichloromethanesulfonic acid, etc., and Lewis acids such as tetraisopropyl titanate. These catalysts can serve the purpose when used in a proportion of 0.1 to 10 wt % to the reaction mixture.

The thus produced (meth)acryl group-containing organosiloxane can be isolated in the following manner: After the dealcoholation and dehydration steps are completed, the reaction product is cooled, optionally subjected to a treatment with active carbon or the like, and then undergoes filtration or a like operation to remove the cation exchange resin.

The reactions described above can be carried out in an organic solvent, too. Suitable examples of a solvent usable therein include aromatic hydrocarbons such as toluene, xylene, etc., aliphatic hydrocarbons such as hexane, isooctane, etc., ketones such as methyl ethyl ketone, methyl isobutyl ketone, etc., and esters such as ethyl acetate, etc.

As for the (meth)acryl group-containing organosiloxanes obtained in accordance with the present preparation method, the following compounds are specific examples thereof:

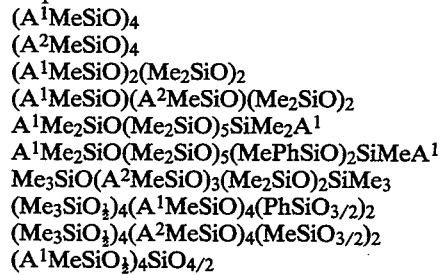

wherein $A^1$ stands for the group of $CH_2=CHCOO(CH_2)_3-$, $A^2$ the group of $CH_2=C(CH_3)COO(CH_2)_3-$, Me the group of $CH_3-$, and Ph the group of $C_6H_5-$.

According to embodiments of the preparation method of the present invention, only the alkoxy groups are selectively hydrolyzed, while the ester linkage in the (meth)acryl group does not undergo hydrolysis. This is due to the use of a cation exchange resin as an acid catalyst, as described above in detail. Thus, the preparation can be carried out with ease in one reaction vessel and, what is more, the acryl group-containing organosiloxanes prepared in accordance with the present invention are much higher in purity and yield rate than those obtained by the conventional method using a highly nucleophilic acid as an acid catalyst.

The present invention will now be illustrated in more detail by reference to the following examples. However, the invention should not be construed as being limited to these examples.

EXAMPLE 1

In a four-neck flask equipped with a stirrer, a thermometer, a reflux condenser and a dropping funnel were placed 323 parts of a silane compound of formula, $CH_2=CHCOO(CH_2)_3Si(CH_3)(OCH_3)_2$, and 3.2 parts of a cation exchange resin [Amberlite 200C (H+type), trade name, products of Organo Co., Ltd.].

Then, 35 parts of water was dropped into the flask at room temperature as the temperature inside the flask was controlled to 40° C. using an oil bath. At the conclusion of the dropping, the inside temperature of the flask was raised to 70° C., thereby distilling out the methanol produced by the reaction. Further, the inside temperature of the flask was raised to 110° C. to distill out the excess water.

After the conclusion of the removal by distillation, the reaction mixture was cooled, and the cation exchange resin was filtered out. Thus, 248 parts of the product was obtained. By the analyses of its IR spectrum, $^1$H NMR spectrum and gel permeation chromatogram, the product obtained was confirmed to be the acryl group-containing siloxane represented by the formula, $[CH_2{=}CHCOO(CH_2)_3Si(CH_3)O]_4$. Thus, the yield of 97% was achieved.

EXAMPLE 2

Another product (248 parts) was obtained in the same manner as in Example 1, except that the silane compound as a starting material was changed to 344 parts of a silane compound of formula, $CH_2{=}C(CH_3)COO(CH_2)_3Si(CH_3)(OCH_3)_2$. The obtained product underwent the same analyses as in Example 1, thereby confirming it to be the methacryl group-containing siloxane represented by the formula, $[CH_2{=}C(CH_3)COO(CH_2)_3Si(CH_3)O]_4$. Thus, the yield of 90% was achieved.

EXAMPLE 3

Still another product (165 parts) was obtained in the same manner as in Example 1, except that the silane compound as a starting material was changed to a mixture of 162 parts of a silane compound of formula, $CH_2{=}CHCOO(CH_2)_3Si(CH_3)(OCH_3)_2$, and 89 parts of an alkoxy group-containing silane compound of formula, $(CH_3)_2Si(OCH_3)_2$. The obtained product underwent the same analyses as in Example 1, thereby confirming it to be the acryl group-containing siloxane represented by the formula, $[CH_2{=}CHCOO(CH_2)_3Si(CH_3)O]_2[(CH_3)_2SiO]_2$. Thus, the yield of 90% was achieved.

EXAMPLE 4

A further product (392 parts) was obtained in the same manner as in Example 1, except that the silane compound as a starting material was changed to a mixture of 327 parts of a silane compound of formula, $CH_2{=}CHCOO(CH_2)_3Si(CH_3)(OCH_3)_2$, 156 parts of an alkoxy group-containing silane compound of formula, $(CH_3)_3Si(OCH_3)$, and 68 parts of an alkoxy group-containing silane compound of formula, $CH_3Si(OCH_3)_3$, the amount of the cation exchange resin used was changed to 5.5 parts and the amount of water used was changed to 65 parts. The obtained product underwent the same analyses as in Example 1, thereby confirming it to be the acryl group-containing siloxane represented by the formula,

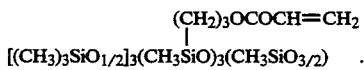

Thus, the yield of 95% was achieved.

COMPARATIVE EXAMPLE 1

The hydrolysis reaction was carried out in the same manner as in Example 1, except that 1.6 parts of conc. sulfuric acid was used as acid catalyst in place of the cation exchange resin. After the completion of the reaction, methanol and water were removed from the reaction mixture. Then, sodium carbonate (4.8 parts) was added, and the stirring was continued for 2 hours at 110° C. The resulting reaction mixture was cooled, and filtered off. Thus, an product (205 parts) was obtained.

The obtained product underwent the same analyses as in Example 1, thereby confirming it to be the siloxane compound having the formula, $[CH_2{=}CHCOO(CH_2)_3Si(CH_3)O]_{3.1}[OH(CH_2)_3Si(CH_3)O]_{0.9}$.

The foregoing formula indicates that about 22.5% of the acryl moieties, $CH_2{=}CHCOO{-}$, were converted to $-OH$ groups by hydrolysis. That is, it has proved that the hydrolysis using sulfuric acid (or a highly nucleophilic acid) involved a great deal of side reaction.

What is claimed is:

1. A method of preparing (meth)acryl group-containing organosiloxanes, comprising selectively hydrolyzing in the presence of water only the alkoxy group or groups of a (meth)acryl group-containing alkoxysilane compound in the presence of a cation exchange resin as an acid catalyst.

2. The method of claim 1, wherein the (meth)acryl group-containing alkoxysilane compound is chosen from the compounds represented by the following formula:

$$A_a SiR^1{}_b (OR^2)_c$$

wherein A represents a monovalent hydrocarbon radical containing a (meth)acryl group; $R^1$ represents an alkyl group containing 1 to 10 carbon atoms or an aryl group; $R^2$ represents an alkyl group containing 1 to 6 carbon atoms; and "a" and "c" are each an integer of from 1 to 3 and "b" is 0, 1 or 2, provided that a+b+c is 4.

3. The method of claim 2, wherein A is a group of formula, $CH_2{=}CR^3COO(CH_2)_d{-}$, wherein $R^3$ is a hydrogen atom or a methyl group, and "d" is an integer of from 1 to 6.

4. The method of claim 3, wherein A is $CH_2{=}CHCOO(CH_2)_3{-}$, $CH_2{=}C(CH_3)COO(CH_2)_3{-}$, $CH_2{=}CHCOOCH_2{-}$ or $CH_2{=}C(CH_3)COOCH_2{-}$, $R^1$ is a methyl, ethyl or phenyl group, $R^2$ is a methyl, ethyl or propyl group, and "a" is 1.

5. The method of claim 1, wherein the cation exchange resin is present in an amount of from 0.1 to 20 parts per 100 parts of the alkoxysilane compound and the water is present in an amount of from 1 to 200 parts per 100 parts of the alkoxysilane compound.

6. The method of claim 1, wherein the (meth)acryl group-containing alkoxysilane compound is mixed with one or more other alkoxy group-containing silane compounds.

7. The method of claim 6, wherein the other alkoxy group-containing silane compound is chosen from the compounds represented by the formula, $R^1{}_{(4-e)}Si(OR^2)_e$, wherein $R^1$ represents an alkyl group containing 1 to 10 carbon atoms or an aryl group, $R^2$ represents an alkyl group containing 1 to 6 carbon atoms, and e is an integer of from 1 to 4.

8. The method of claim 1, wherein the cation exchange resin is an $H^+$ cation exchange resin.

9. The method of claim 1, wherein, after the hydrolysis, the alcohol produced by the hydrolysis and the excess water are removed by distillation and a condensation reaction occurs between the SiOH and Si alkoxy groups remaining in the reaction system.

10. The method of claim 1, wherein the product (meth)acryl group-containing organosiloxanes is selected from the group consisting of $(A^1MeSiO)_4$,
$(A^2MeSiO)_4$,
$(A^1MeSiO)_2(Me_2SiO)_2$,
$(A^1MeSiO)(A^2MeSiO)(Me_2SiO)_2$, $A^1Me_2SiO(Me_2SiO)_5SiMe_2A^1$,
$A^1Me_2SiO(Me_2SiO)_5(MePhSiO)_2SiMeA^1$,
$Me_3SiO(A^2MeSiO)_3(Me_2SiO)_2SiMe_3$,
$(Me_3SiO_{\frac{1}{2}})_4(A^1MeSiO)_4(PhSiO_{3/2})_2$,
$(Me_3SiO_{\frac{1}{2}})_4(A^2MeSiO)_4(MeSiO_{3/2})_2$, and $(A^1MeSiO_{\frac{1}{2}})_4SiO_{4/2}$ wherein $A^1$ stands for the group $CH_2\!\!=\!\!CHCOO(CH_2)_3\!-$, $A^2$ the group $CH_2\!\!=\!\!C(CH_3)COO(CH_2)_3\!-$, Me the group $CH_3\!-$, and Ph the group $C_6H_5$.

* * * * *